United States Patent
Durkacz et al.

(10) Patent No.: US 10,851,077 B2
(45) Date of Patent: Dec. 1, 2020

(54) METHOD FOR EXTRACTING COMPOSITIONS FROM PLANTS

(71) Applicant: World Class Extractions, Inc., Toronto (CA)

(72) Inventors: Anthony J. Durkacz, Toronto (CA); Mark T. Cullen, Orange City, FL (US)

(73) Assignee: WORLD CLASS EXTRACTIONS INC., Burnaby (CA)

( * ) Notice: Subject to any disclaimer, the term of this patent is extended or adjusted under 35 U.S.C. 154(b) by 77 days.

(21) Appl. No.: 16/265,768

(22) Filed: Feb. 1, 2019

(65) Prior Publication Data

US 2019/0241536 A1 Aug. 8, 2019

Related U.S. Application Data

(60) Provisional application No. 62/627,616, filed on Feb. 7, 2018.

(51) Int. Cl.
| | |
|---|---|
| *C07C 37/68* | (2006.01) |
| *C07D 311/80* | (2006.01) |
| *C07C 37/74* | (2006.01) |
| *C07C 37/70* | (2006.01) |
| *C07C 37/00* | (2006.01) |

(52) U.S. Cl.
CPC .......... *C07D 311/80* (2013.01); *C07C 37/004* (2013.01); *C07C 37/685* (2013.01); *C07C 37/70* (2013.01); *C07C 37/74* (2013.01); *C07C 2601/16* (2017.05)

(58) Field of Classification Search
CPC .................................................. C07C 37/68
See application file for complete search history.

(56) References Cited

U.S. PATENT DOCUMENTS 8,445,034 B1  5/2013  Coles

FOREIGN PATENT DOCUMENTS

| CN | 104277917 | 1/2015 |
| CN | 106831353 | 6/2017 |
| CN | 106860492 | 6/2017 |
| CN | 106860492 A1 * | 6/2017 |

OTHER PUBLICATIONS

CN 106860492 A1 (published Jun. 2017), referenced in IDS of Jun. 13, 2019, with ProQuest machine-generated English-language translation provided. (Year: 2017).*

Hielscher. "Highly Efficient Cannabidiol (CBD) Extraction from Cannabis." (2019). Accessed Sep. 15, 2019. Available from: < https://www.hielscher.com/highly-efficient-ultrasonic-cannabidiol-cbd-extraction-from-cannabis.htm >. (Year: 2019).*
Pryor, Ezra; The Perfect Solvent for Cannabis Extraction; Nov. 20, 2016; 2 pages; CANNABIZ Journal.
Li, Tao et al; A Saponification Method for Chlorophyll Removal from Microalgae Biomass as Oil Feedstock; Sep. 7, 2016 (on-line https://www.ncbi.nlm.nih.gov/pmc/articles/PMC5039533/); 26 pages; Mar Drugs (Sep. 2016; 14 (9):162).
Young, Lee W.; PCT International Search Report and Written Opinion; dated Apr. 24, 2019; 8 pages; Alexandria, Virginia.
MD Range; Seepex Gmbh; 2019 [retrieved 2018];Retrieved from the Internet: https://www.seepex.com/us/pumps-and-control-systems/metering-pump/md-range/?no_cache=1.
Ultimate Herb Dryer; Viagrow; 2019 [retrieved 2018]; Retrieved from the Internet: https://www.atlantishydroponics.com/product-p/vuhd1.htm.
Harvester Pro Five-tier Dehydrator User Manual; Cabela; date of manual unknown [retrieved 2018]; Retrieved from Internet: https://www.cabelas.com/product/CABELAS-HARVESTER-PRO-TIER-DEHYDRATOR/2122098.uts.
ECOPURE Solvent Recyclers (Press Release); PPC Technologies & Solutions LLC; Aug. 5, 2011 [retrieved 2018]; Retrieved from Internet: https://www.ppcts.com/pr12.htm.
10 Tray Dehydrator User Manual; Cabela; Jun. 8, 2016 [retrieved 2018]; Retrieved from Internet: https://www.cabelas.com/assets/product_files/pdf/541646_Six_Tray_Heavy_Duty_Dehydrator.pdf.
Flowtron LE-900 Ultimate Mulcher Electric Leaf Shredder Owner's Manual; Flowtron; Oct. 19, 2011 [retrieved 2018]; Retrieved from Internet: https://www.flowtron.com/manuals/357%203151%20REV%2011%20LE-900%208pg%20OM.pdf.
Eco-Shredder Owners Operating Manual Chipper / Shredder / Mulcher; Durostar; Feb. 2, 2012 [retrieved 2018]; Retrieved from Internet: https://www.amleo.com/images/art/es1600-manual.pdf.

* cited by examiner

*Primary Examiner* — John S Kenyon
(74) *Attorney, Agent, or Firm* — Stetina Brunda Garred and Brucker

(57) ABSTRACT

Methods for extracting and concentrating cannabinoids using ultrasound-enhanced solvent extraction. Freshly harvested cannabis plant materials, which may be selectively chosen plant parts or the entire plant itself, are shredded to a particular particle size. The plant material is then mixed with a solvent to form a slurry, and thereafter subjected to ultrasound to release intracellular contents into the solvent. Filtering steps are then applied to remove biomass, waxes and chlorophyll. Water removal and solvent recovery steps are further applied to ultimately derive an extract having high concentrations of target cannabinoids, and in particular cannabidiol (CBD). The methods may be deployed on-site in batch or continuous flow processes, and may further be utilized to derive other types of materials from plants, such as essential oils.

22 Claims, 6 Drawing Sheets

METHOD FOR EXTRACTING COMPOSITIONS FROM PLANTS

CROSS-REFERENCE TO RELATED APPLICATIONS

This application relates to and claims the benefit of U.S. Provisional Application No. 62/627,616 filed Feb. 7, 2018 and entitled "METHODS FOR EXTRACTING COMPOSITIONS FROM PLANTS," the entire disclosure of which is hereby wholly incorporated by reference.

STATEMENT RE: FEDERALLY SPONSORED RESEARCH/DEVELOPMENT

Not Applicable

BACKGROUND

The present invention relates to methods for extracting and concentrating cannabinoids and other target compounds from cannabis using ultrasound-enhanced solvent extraction. The methods of the present invention are exceptionally effective in maximizing the recovery of target cannabinoids, and in particular cannabidiol (CBD), from either select plant structures of cannabis, and in particular the roots thereof, or from the entire cannabis plant as a whole. It is further believed that the methods of the present invention may likewise be exceptionally effective in extracting essential oils and fragrance extracts from plants for use in a variety of scented products, perfumes and other applications.

Techniques for deriving extracts from plants, and in particular cannabis, are well-known in the art. Indeed, crude methods for deriving extracts from cannabis date back more than a thousand years ago. To that end, the primary objective in deriving such extracts is to isolate cannabinoids, namely, the chemical compounds secreted by cannabis that imitate naturally-produced endocannabinoids that maintain homeostasis and general health and well-being.

Cannabis contains at least 85 types of cannabinoids with each having a different therapeutic effect in treating pain, nausea, anxiety and inflammation, among others. When cannabis is consumed, whether through consumption or inhalation (as in smoking), the cannabinoids, usually following decarboxylation, are operative to bind to receptor sites either located in the brain, via CB-1 receptors, or peripherally throughout the body, via CB-2 receptors. The most well-known and studied of the cannabinoids include tetrahydrocannabinol (THC) and cannabidiol (CBD), whose respective chemical structures are shown below:

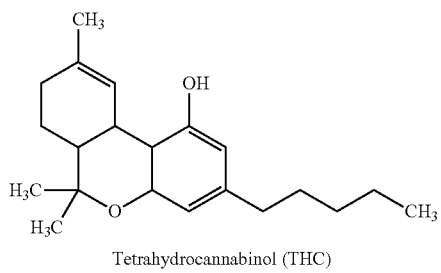

Tetrahydrocannabinol (THC)

-continued

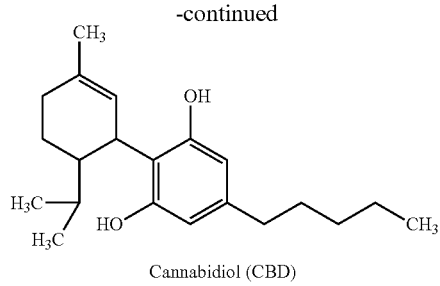

Cannabidiol (CBD)

THC is well-known as a psychoactive or hallucinogenic compound that binds primarily to CB-1 receptors and is responsible for producing the euphoric high associated with cannabis consumption. CBD, on the other hand, is non-psychoactive cannabinoid and binds primarily to CB-2 receptors throughout the body and is associated with reducing anxiety, reducing pain and protecting against nerve damage, among other physiological effects. Other known cannabinoids and their derivatives that also have potentially therapeutic applications include the following:

Cannabigerolic Acid (CBGA)
Cannabigerolic Acid Monoethylether (CBGAM)
Cannabigerolic (CBG)
Cannabigerolic Monoethylether (CBGM)
Cannabigerovarinic Acid (CBGVA)
Cannabigerovarin (CBGV)
Cannibichromenic Acid (CBCA)
Cannibichromene (CBC)
Cannibichromevarinic Acid (CBCVA)
Cannibichromevarin (CBCV)
Cannabidiolic Acid (CBDA)
Cannabidiol Monoethylether
Cannabidiol-C4 (CBD-C4)
Cannabidivarinic Acid (CBDVA)
Cannabidivarin (CBDV)
Cannabidiorcol (CBS-C1)
Delta-9-tetrahyrocannabinolic Acid A (INPLANTA A-A)
Delta-9-tetrahyrocannabinolic Acid B (INPLANTA A-B)
Delta-9-tetrahyrocannabinol (INPLANTA)
Delta-9-tetrahyrocannabinol-C4 (INPLANTA-C4)
Delta-9-tetrahyrocannabivarin (INPLANTA V)
Delta-9-tetrahyrocannabiorcolic Acid (INPLANTA A-C1)
Delta-9-tetrahyrocannabiorcol (INPLANTA-C1)
Delta-7-cis-iso-tetrahyrocannbivarin
Delta-8-tetrahyrocannabinolic Acid (8-INPLANTA A)
Delta-8-tetrahyrocannabinol (8-INPLANTA)
Cannabicyclolic Acid (CBLA)
Cannabicyclol (CBL)
Cannabicyclovarin (CBLV)
Cannabielsoic Acid A (CBEA-A)
Cannabielsoic Acid B (CBEA-B)
Cannabielsoin (CBE)
Cannabinolic Acid (CBNA)
Cannabinol (CBN)
Cannabinol Methylether (CBNM)
Cannabinol-C4 (CBN-C4)
Cannabivarin (CBV)
Cannabinol-C2 (CBN-C2)
Cannabiorcol (CBN-C1)
Cannabinodiol (CBND)
Cannabinodivarin (CBVD)
Cannabitriol (CBT)

10-Ethoxy-9-hydroxy-delta-6a-tetrahyrocannabinol
8,9-Dihydroxy-delta-6a-tetrahyrocannabinol
Cannabitriolvarin (CBTV)
Ethoxy-cannabitriolvarin (CBTVE)
Dehydrocannabifuran (DCBF)
Cannabifuran (CBF)
Cannabichromanon (CBCN)
Cannabicitran (CBT)
10-Oxo-delta-6a-tetrahyrocannabinol (OINPLANTA)
Delta-9-cis-tetrahydrocannbinol (cis-INPLANTA)
3,4,5,6-Tetrahydro-7-hydroxy-alpha-alpha-2-trimethyl-9-n-propyl-2,6-methano-2H-1-benzoxocin-5-methanol (OH-iso-HHCV)
Cannabiripsol (CBR)
Trihydroxy-delta-9-tetrahyrdocannabinol (triOH-IN-PLANTA)

Recovering the sought-after cannabinoids from the cannabis plant is a well-known and challenging process that to be performed most effectively requires substantial time and labor involving numerous steps. In this regard, most extraction processes require careful harvesting of select portions of the cannabis plant, and, in particular the leaves and buds that, once removed, must be subjected to a time-consuming drying process whereby the moisture content of the plant, typically around 75% moisture when harvested, is dried to have a resultant moisture content of 10-15%. Because cannabinoids can easily decompose when subjected to heat and UV radiation, rapid drying techniques are often times highly destructive and can cause a significant portion of the sought-after cannabinoids to chemically decompose. There are currently no commercially-viable methods for rapidly and easily deriving cannabinoid extracts in high concentrations from freshly-harvested cannabis, and much less methods that are portable and can be deployed on a specific grow site.

Still further, even if properly harvested and cured cannabis is obtained, the cannabinoids contained therein must be subjected to a separate extraction process. Many such extraction methods are well-known in the art, including simple water-based extraction, which typically utilizes water, heat and pressure through a filtering mechanism. Alternatively, cannabinoids can be derived through solvent-based extraction processes, which typically deploy the use of alcohols and other hydrocarbons, most notably hexane, butane and propane. Still further, supercritical $CO_2$ can be used as a solvent to derive cannabis extracts.

Problems associated with both water and solvent-based extraction processes are well-known. Water-based extracts are known to be significantly diluted as many of the cannabinoids are never ultimately recovered from the cannabis plant. Solvent-based extracts, while deriving more potent extracts, typically use toxic and potentially explosive solvents that are dangerous to work with. Moreover, residual solvent can and does frequently appear in the final cannabis extract which can make the extract dangerous to consume. Both water and solvent-based extracts further suffer from the drawback of suboptimal cannabinoid extraction due to the inability to draw out intracellular cannabinoids that are typically trapped within the cell walls of the cannabis plant material, and hence unable to be recovered. Both extraction processes further disadvantageously can produce extracts having residual components, such as waxes, fatty acids and chlorophyll, which make for an undesirable product and require further processing to derive an extract only containing the cannabinoids of interest.

While other modalities have been deployed in combination with the aforementioned extraction techniques to increase cannabinoid yield and minimize residual contaminants and excess solvent and the like, there has not heretofore been a comprehensive method by which an extract can ultimately be derived that includes a maximum concentration of cannabinoids that can be isolated from all or part of a cannabis plant, including roots, seeds and other parts of the cannabis plant deemed undesirable, that further minimizes the presence of undesirable contaminants and volume of solvent associated with such extraction processes. There is much less any such process that can further be directly utilized on freshly harvested cannabis of any variety, including all species of hemp, that does not need to first undergo extensive and time consuming drying processes, can be designed to be portable in nature, can be deployed on-site in close proximity to where the cannabis is grown and directly harvested, and can likewise be deployed in batch or continuous flow applications.

BRIEF SUMMARY

The present invention specifically addresses and alleviates the above-identified deficiencies in the art. In this regard, the present invention is directed to systems and processes for extracting and concentrating target compositions from plants, and in particular cannabinoids from cannabis especially CBD and derivatives thereof, although other specific cannabinoids may likewise be targeted for extraction. To that end, the present invention contemplates using freshly harvested cannabis, that can include the entire plant, including roots, stems, leaves, buds and seeds among other structures, or specific parts of the plant, namely, buds, and process the same despite the presence of water present in such freshly harvested plant material. In one application, it is contemplated that the roots of the cannabis plant may be exclusively utilized as the source of the material from which the cannabinoids are extracted. The methods of the present invention are further operative to extract cannabinoids from all species of cannabis, which as used herein expressly including (e.g., cannabis) sub species, i.e., indica, sativa, ruderalis, and further expressly includes hemp and all parts thereof (e.g., seeds) as presently defined as containing >0.3% THC per volume concentration.

Such freshly-harvested plant material is first shredded or grinded to a particular particle size ranging from 1-12 mm, and preferably 2-6 mm, or are alternatively sized such that the pieces are operative to pass through a 0.5 inch mesh screen and preferably through a 0.25 inch mesh screen. With respect to the shredding step, in some embodiments a two (2) step process is contemplated depending on what part of the plant is being processed. For softer portions of the plant, such as leaves and buds, that can be readily processed into the desired particulate size using food-grade, medical plant processors. For the processing of the thicker, more dense plant material, and in particular the roots and stems, it is contemplated that processing techniques will be utilized that will be modeled after root-type vegetable processing where a heavy duty shredder is utilized to shred the denser plant material into a first particle size and thereafter passed to a second food-grade-type processor so as to achieve a desired particle size.

To that end, it is believed that a variety of conventional shredding mechanisms and techniques may be deployed. In certain embodiments, it is believed that low speed shredding of the cannabis material may be utilized using conventional food grade processing equipment or, for larger volumes of plants material, spiral coil or screw-type shredders. In more highly refined embodiments, cryomilling may be deployed whereby the shredded plant material either before or during the shredding step is subjected to liquid nitrogen to thus enable plant material to be frozen for easier shredding and subsequent processing when mixed with solvents. For example, the cannabis plant material may be deposited into a bowl cutter/agitation tank where the temperature is controllable and the cannabis is cut to size in cryogenic conditions. The shredded cannabis may likewise be subjected to liquid nitrogen after the shredding step so as to reduce temperature of the plant material prior to further processing so as to facilitate the removal of impurities, such as waxes and chlorophyll.

Once sufficiently shredded to the ideal particle size, the particulate cannabis plant material is then mixed with a solvent, which can include any of a variety of known liquid hydrocarbon solvents, including ethanol, isopropyl alcohol, coconut oil, glycerin, and propylene glycol, as well as super critical $CO_2$ or water. Presently, it is believed ethanol is preferred. In certain embodiments, an ideal solvent includes 1,1,1,2-tetrafluoroethane, which is also known as hydrofluorocarbon (HFC)-134a. The particulate cannabis plant material is mixed with the solvent such that the amounts of solvent to ground cannabis plant material will range from 25 mL of solvent to 50 grams of particulate cannabis to 25 mL of solvent per 0.01 gram of particulate cannabis with the range of 25 mL of solvent per 10 grams of cannabis to 25 mL of solvent per 2 grams of cannabis being preferred, especially for hemp extractions, and in a further preferred refinement will range between 25 mL per 10 grams to 25 mL per 3 grams. A ratio of 25 mL per 5 grams for all varieties of cannabis, including hemp, is believed to be most ideally suited for the practice of the present invention.

In all applications, the solvent is preferably maintained in a chilled state but can be utilized in a range from preferably between −80 to 95° C., and mixed with the plant material to form a slurry. When using ethanol, the temperature range is preferably between −40 to −60° C. Such slurry is then subjected to ultrasound, the latter being applied at a frequency ranging from 5 kHz-1 MHz with the general range of 10 kHz-60 kHz being preferred and 40 kHz being most preferred. Such sonic energy will further be applied with a displacement amplitude in the range from about 20-100 micrometers, with 80 micrometers being most preferred, and with power being delivered in a range from 90 to about 160 watts per square centimeter of liquid slurry being treated. To that end, an ultrasound generator or sonicator having a power output ranging from 200 to 2000 watts can typically be utilized with a generator having an out form 1000-2000 watts being preferred for treating larger volumes. The ultrasound will further preferably be applied for a duration ranging from 30 seconds to a maximum of 5 minutes, with up to 120 seconds being preferred. The slurry is preferably maintained at a temperature of −40° C. or less when the ultrasound is applied and ethanol is used as a solvent.

The ultrasound-treated slurry is then filtered and treated to remove chlorophyll and other undesirable components through a variety of mechanisms, and further treated to remove the solvent and residual water emanating from the shredded, freshly harvested cannabis plant to derive an oil-based extract. In optional refinements of the invention, the slurry following treatment with ultrasound may be processed to facilitate the removal of plant biomass, such as through a French press or centrifugation step, with the resultant waste biomass being treated further with ultrasound to reduce mass volume. It is also contemplated that an on-going solvent recovery application may be integrated into the processes of the present invention, especially following post-ultrasound treatment of the slurry, and can include EVAP/vacuum recovery and boiling recovered solvent through a distillation system that not only remove the solvent but also remove any water emanating from the harvested cannabis plant.

In alternative processing embodiments, after sonication, the slurry is passed through a screw plate filter to separate the liquid containing ethanol, water, chlorophyll, wax and oil components, the latter containing the desired cannabinoids. The spent solid biomass is separated for disposal or is recycled or repurposed. The waxes and chlorophyll may be removed by convention means. Alternatively, the chlorophyll may be removed by a unique sequential application of micro/nano membrane filtration and activated carbon.

The oil-based extracts of cannabis may then be derived by specialized wiped-film evaporation/thin film evaporators or thin film filtration. With respect to the former, it is contemplated that conventional wiped-film evaporation may be deployed whereby the oil-based cannabis extract is caused to be distributed as a film on the inner surface of a heated pipe whereby an integrated wiping system, typically a rotor, is operative to generate a highly turbulent flow, which thus results in the formation of bow waves and creating optimum heat flux and mass transfer conditions. The volatile components, namely, any water (as may be present from shredding the harvested plant) and solvent present in the slurry, are rapidly evaporated via conductive heat transfer whereby the vapors exit a vapor discharge section and are subsequently condensed and separated.

With respect to thin film filtration, such procedure involves the use of a micron pressure filter having a cloth filter medium to remove fine particulates suspended in the slurry following the application of ultrasound. This filter is intended to remove chlorophyll in a series of micro and nano porous ceramic membranes whereby a series of membrane filtration techniques covering microfiltration to remove colloidal matter, tight ultrafiltration or nano-filtration will reduce the color intensity imparted majorly by chlorophyll A and chlorophyll B and to a minor extent by other forms of the coloring matter. In large volume applications, it is contemplated that two or more identical filters are run in parallel so that during operation one can be bypassed while the other is changed supporting continuous operation. Ultimately, the oil component containing the cannabinoids will pass along with the solvent and can be recovered per conventional techniques.

In all cases, the resultant extract contains an exceptionally high concentration of cannabinoids, and in particular CBD's that can be quantified by UV-vis absorbent spectroscopy, among other techniques. Furthermore, all of the equipment operative to perform the aforementioned steps of the process of the present invention is generally commercially available and portable in nature such that the various steps of shredding/grinding, slurry formation, treatment with ultrasound, filtering and concentrating the extract ultimately derived can readily be transported and deployed to a growth site where freshly harvested cannabis can be treated and processed immediately. Moreover, the methods of the present invention expressly contemplate processing in either a batch or continuous flow process and may be scaled to accommodate any range of weight or field size of cannabis plant material. The methods of the present invention are further contemplated as being exceptionally efficient and effective at deriving extracts from other plants, such as essential oils and fragrance compounds as produced by a wide variety of plants. In this regard, it is believed that the methods of the present invention can be useful in deriving fragrant extracts for use in a wide variety of products, such as perfumes, cosmetics, and other areas requiring or desiring fragrance enhancements.

BRIEF DESCRIPTION OF THE DRAWINGS

These as well as other features of the present invention will become more apparent upon reference to the drawings.

DETAILED DESCRIPTION

The present invention is directed to methods for extracting and concentrating desired cannabinoids, and in particular CBD, from cannabis plant material that are not only operative to maximize the amount of desired cannabinoids derived from cannabis but to further do so in a manner that is far more effective and efficient than prior art methods. In particular, the methods of the present invention advantageously enable "wet" or freshly harvested cannabis to be processed immediately on-site through a combination of commercially-available mechanisms, and can further be deployed to extract cannabinoids in high concentrations from all parts of the cannabis plant, and in particular the roots of such plant. While it is believed that any of a variety of well-known cannabis plants can be utilized, and in particular either cannabis indicia or *Cannabis sativa*, it is believed that *Cannabis sativa* may be deemed more optimal due to its higher levels of CBD, as opposed to the psychoactive and intoxicating THC component. As should be understood, other varieties of cannabis may be chosen based on the desired cannabinoid sought to be derived. In this regard, for purposes of the present invention, the term "cannabis" should be construed to encompass all species of cannabis, including sub species, i.e., indica, sativa, ruderalis, and expressly includes hemp and all parts thereof (e.g., seeds) as presently defined as containing >0.3% THC per volume concentration.

Figure 1:
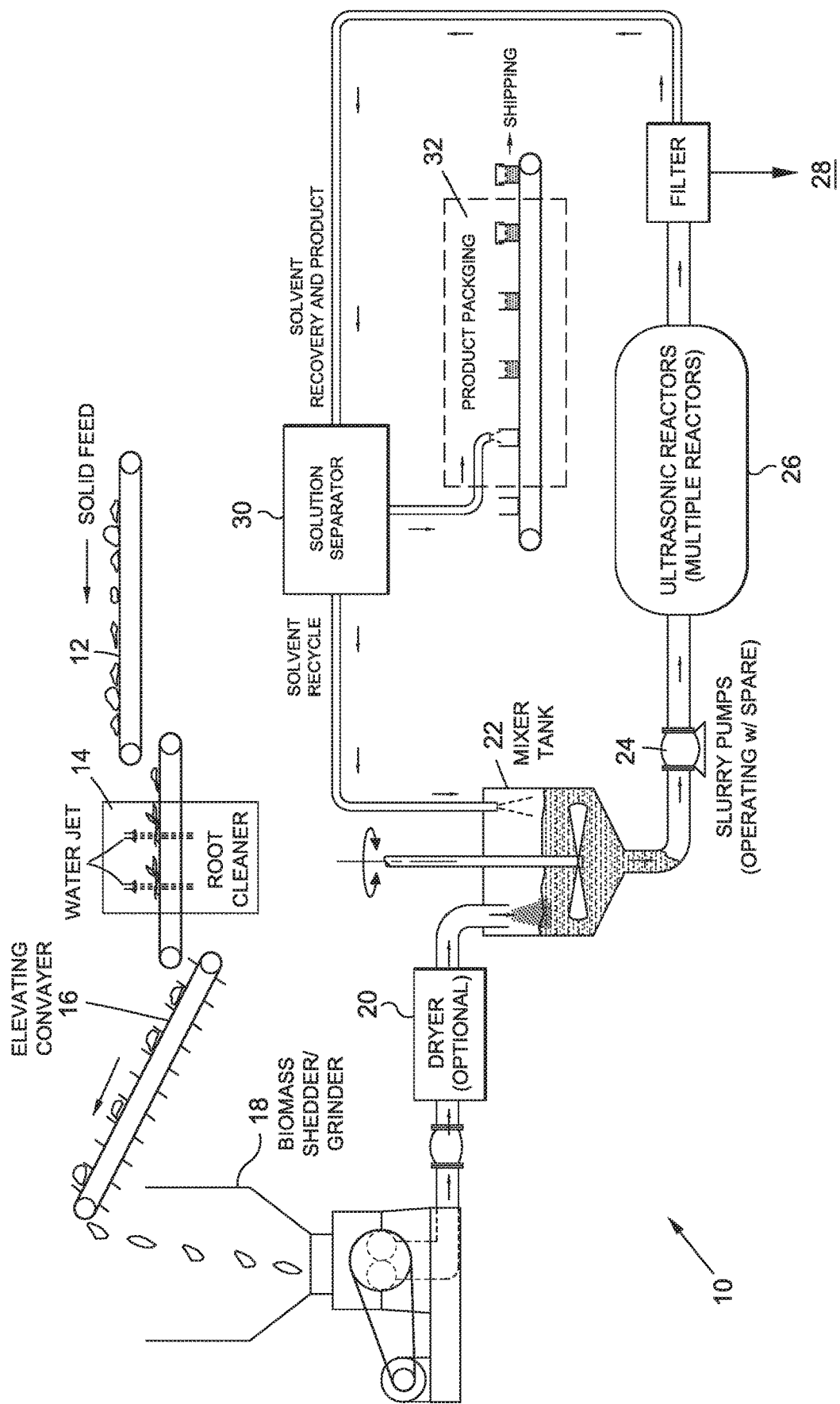
FIG. 1 shows a flow chart of the steps and system components for performing the methods for extracting and concentrating cannabinoids from cannabis per a first embodiment of the present invention.

According to a first preferred method and system 10 shown in FIG. 1, a solid feed of cannabis plant material 12 from a desired species of cannabis is provided, preferably freshly harvested, and fed to a conveyer 16 and ultimately to shredder 18 where the cannabis is shredded or grinded to have a particulate size ranging from 1 to 12 mm and preferably 2-6 mm. The particles are alternatively cut to size such that they are operative to pass through a 0.5 inch mesh screen, and preferably through a 0.25 inch mesh screen.

Such shredding can be accomplished via a variety of conventional shredding machines, such as the Eco-Shredder ES1600 14-Amp Electric Chipper/Shredder/Mulcher produced by Durostar of La Verne, Calif. and the Flowtron LE-900 Ultimate Mulcher Electric Leaf Shredder produced by Flowtron of Malden, Mass.

While it is believed that the particulate size can be readily achieved utilizing food-grade, medical plant processors well-known in the art, in some applications that involve the processing of thicker-more dense plant material, in particular the roots and stems of the cannabis plant, the present invention may integrate processing techniques modeled after root-type vegetables processing. To that end, it is contemplated that the cannabis plant will typically be harvested by hand and must be first washed to remove dirt such as by root cleaner 14. To perform such step, it is contemplated that any variety of brush washer machines for fruit and vegetable washing may be readily utilized. As is well-known in the art, such machines are specifically designed to wash and rinse off dirt from freshly harvested vegetables. Following such washing process, a first heavy-duty shredder is utilized to break down the plant's structures to a first smaller particulate size. Thereafter, if necessary, such pre-shredded plant structures are subjected to the aforementioned food-grade, medical plant processors as so to achieve the desired uniformed size. As will be appreciated by those skilled in the art, such processing can be done using conventional equipment that is commercially available at relatively low cost.

Advantageously, the methods of the present invention contemplate immediate processing of freshly harvested cannabis on-site and are operative to derive extracts that further remove water naturally present in the cannabis plant by virtue of being freshly harvested. However, in some alternative embodiments, the cannabis plant material may optionally be first cured and dried via dryer 20 such that the moisture content of the cannabis material reaches as low as 10-15%, per conventional drying and curing procedures. To that end, it is believed that a variety of conventional drying mechanisms and techniques may be deployed including the use of dehydrators such as the Ultimate Herb Dryer systems produced by Viagrow or Cabela's Harvester Pro Five-tier Dehydrator or Cabela's 6 or 10 tray Dehydrators produced by Cabela. It is likewise contemplated that conventional freeze-drying techniques, technically known as lyophilisation, lyophilization, or cryodesiccation, may be utilized to pre-treat the cannabis/hemp plant materials. Importantly, it is contemplated that all such plant material may include any part of the cannabis or hemp plant, including stems and seeds, in addition to the traditionally sought-after leaves and buds. Furthermore, the present invention expressly contemplates utilizing the root of the cannabis plant as part of deriving the extract of the present invention, and may exclusively utilize the root material of the plant.

In certain applications to facilitate the shredding of the plant material to the desired particulate size, it is contemplated that conventional low speed shredding techniques may be deployed as understood by those skilled in the art. Alternatively, cryomilling applications may be utilized whereby the plant material is subjected to liquid nitrogen either before or during the shredding process. As it will be appreciated by those skilled in the art, by deploying such cryomilling procedures allows for more thorough and uniformed shredding for a greater consistency in uniformed particle size. For example, the step of cryomilling can happen in a bowl cutter or on a conveyer belt system where the pre-frozen cannabis is shredded prior to further processing. Moreover, it is contemplated that the use of liquid nitrogen may be deployed even after the shredding of plant material to thus reduce the plant material temperature as is considered ideal for future processing, discussed more fully below.

Immediately after or concurrently with the shredding and grinding step, a solvent is added to the particulate plant material to form a slurry in mixing tank 22. Such solvent may be selected from any of a variety of known solvents, including those in the group consisting of ethanol, butane, propane, isopropyl alcohol, coconut oil, glycerin, propylene glycol or supercritical carbon dioxide gas, with 100% (200-proof) ethanol being preferred. To the extent an oil solvent is utilized, it will be understood that the volume of the extract ultimately obtained, by virtue of being oil-based, will have a greater volume and more diluted in terms of cannabinoid concentration. Still further, although less desired due to its toxicity, naphtha may also be used as a solvent. Water, either alone or with a phase transfer agent or soap may be used as a solvent as well. A further solvent believed to be particularly well suited for the practice of the present invention includes 1,1,1,2-tetrafluoroethane, also known as hydrofluorocarbon (HFC)-134a. Such halocarbon is known in the art and frequently referenced as a candidate for replacing other halocarbon materials for use in air conditioning and refrigeration systems. Such material also advantageously possesses very low toxicity profile.

The amount of solvent added to the ground cannabis plant material will range from 25 mL of solvent per 50 grams of particulate cannabis to 25 mL of solvent to 0.01 grams of particulate cannabis. A narrower range of 25 mL of solvent per 10 grams of particulate cannabis plant material to 25 mL per 2 grams is preferred, especially for hemp extractions, and in a further preferred refinement between 25 mL solvent per 10 grams particulate cannabis to 25 mL per 3 grams. A ratio of 25 mL of solvent per 5 grams of all varieties of cannabis, including hemp, is believed to be most ideally suited for the practice of the present invention. With respect to the latter ratio, 25 mL per 5 grams, such plant material will preferably consist entirely of cannabis buds, as opposed to any other plant structure. In certain refinements of the present invention, additional additives may be included such as sodium hydroxide in order to facilitate chlorophyll removal through known methods in the art. Exemplary of such methods are disclosed in Li T, Xu J, Wu H, et al. A Saponification Method for Chlorophyll Removal from Microalgae Biomass as Oil Feedstock. Long P, ed. *Marine Drugs*, 2015:14(9):162. Doi:10.2290/md14090162, the teachings of which are incorporated by reference. Such method is believed to be ideal insofar as such method does not cause decarboxylation of the sought-after CBD molecules.

In all applications except for those involving supercritical $CO_2$ or hydrofluorocarbon (HFC)-134a, the solvent as mixed with the plant material will have a temperature ranging from −80 to 95° C.; however, for optimal extraction recovery, the solvent will be kept in a chilled, refrigerated state. Temperatures approaching 0° C. are optimal for water. For ethanol, it is believed that maintaining the temperature between −60 to −40° C. is preferred. Such chilled temperatures may be maintained via the use of conventional techniques and systems such refrigerated baths and/or the use of circulating liquid nitrogen.

The slurry mixture of solvent with particulate plant matter will be mixed for a duration ranging between thirty seconds to ten minutes and is then subjected to ultrasound as delivered through one or more ultrasonic reactors 26. Specifically, the ultrasound will be applied at a frequency ranging from 5 kHz-1 MHz with the general range of 10 kHz-60 kHz being preferred and with 40 kHz being most preferred. Presently, it is believed that the sonic energy applied should have a displacement amplitude in the range of from about 20 to 100 micrometers, with 80 micrometers being most preferred. As should be appreciated, the amplitude may be adjusted according to whether the processes of the present invention are conducted; however, caution should be taken as displacement amplitudes greater than 80 micrometers can cause fluid decoupling to occur.

The preferred range of power that should be delivered should preferably range from about 90 to about 160 watts per square centimeter of slurry treated. The ultrasound will further preferably be applied for a duration ranging from thirty seconds to a maximum of five minutes, with up to one hundred twenty seconds being preferred. When ethanol is used as the solvent, the temperature of the slurry should also preferably be maintained at −40° C. or less when the ultrasound is applied so as to facilitate the subsequent removal of certain contaminants, such as waxes and the like, per conventional winterizing processes well-known to those skilled in the art.

Exemplary equipment operative to impart the ultrasound to such mixture is commercially available from Hielscher USA, Inc. of Wanaque, N.J., although other branded, commercially-available products are contemplated. Typically, ultrasound generators or sonicators having a power output ranging from 200 to 2000 watts can be utilized, with ultrasound generators having an output ranging from 1000 to 2000 watts being well-suited to provide sufficient ultrasonic treatment for the embodiments disclosed herein. Advantageously, the ultrasound applied to the slurry may be done so in either a batch or continuous flow process as may be desired for a given application. The application of ultrasound, as will be readily appreciated, facilitates the disruption of the cell walls of the plant and releases intracellular contents, including the cannabinoids of interest that thus become available for solvent extraction.

Following treatment with ultrasound, the processed crude material will next be passed through a course mesh filter 28 to remove unwanted biomass, with the resultant extract then being treated to remove chlorophyll and other undesirable components, such as fatty acids, waxes and the like. In an exemplary process well suited for the embodiment of FIG. 1, such extract is treated with 0.04% sulfuric acid/phosphoric acid to remove the chlorophyll and other pH labile compounds (e.g., fatty acids, phospholipids, etc.) by precipitation. Once precipitated, the slurry is filtered by a course 100 μm pore size cotton fiber filter. The filtrate is then passed through a 23 μm pore size cellulose acetate filter. The collected filtrate is then treated with an equal volume of 2M sodium hydroxide, to remove any remaining chlorophyll (applicable to applications using butane or propane as a solvent). The organic/aqueous mixture is then passed through a separatory funnel to isolate the organic layer containing the CBDs. To the organic layer-containing the CBDs, 1 gram of magnesium sulfate is added to remove any residual water. Rotary evaporation can then be deployed to remove excess solvent (e.g., ethanol) from the sample. Remaining water can be removed using either an azeotropic distillation, or implementation of anhydrous calcium chloride (desiccant), for removing <5% wt. of water content remaining in the final clear extracted product.

In further refinements of the invention, initial water-removing steps may be performed as part of the harvesting and shredding/grinding phase whereby water may be removed by an azeotropic distillation process. The biomass-extracted filtrate-containing CBDs, a 70% by volume, of cyclohexane is added to the mixture, and distilled at 62.1° C. under vacuum (3000-90 mBar) to remove the cyclohexane and water, leaving the ethanol-containing CBD, or THC. Additional water-removing steps and solvent recovery can likewise be integrated to treat the extract following the application of ultrasound, which may include known azeotropic drying processes and the like. The recovered solvent may also be processed for recycling and continuously utilized in the methods of the present invention in either a batch or continuous flow application.

In a further refinement (not shown), the slurry following treatment with ultrasound may be subjected to a French press whereby the biomass component is compressed from the liquid component. Such technique is well-known in the art and is operative to facilitate the removal of solids from the desired liquid extract. It is likewise contemplated that other solid/liquid separation techniques can be performed to the slurry following treatment with ultrasound, such as centrifugation.

Still further, to address a well-known problem associated with residual biomass, any such biomass, following removal of the desired extract containing the cannabinoids of interest, may separately be treated again with ultrasound to reduce mass volume. Such secondary ultrasound processing may be carried out with the Hielscher systems referenced above and can be performed using known frequencies, power and duration known in the art for treating sewage. An exemplary application could include ultrasonic irradiation from 35 to 130 kHz for different time periods ranging from 5 to 20 minutes at intensity of 50-60 watts per square cm.

It is also expressly contemplated that on-going solvent recovery applications 30 may be integrated into the processes of the present invention, especially following post ultrasound treatment of the slurry. Exemplary techniques include EVAP/vacuum recovery and boiling recovered solvent. With respect to the latter, commercially available systems operative to facilitate solvent recovery include ECOPURE Solvent Recyclers produced by PPC Technologies & Solutions LLC of Pewaukee, Wis. Advantageously, all of the aforementioned equipment referenced above is portable in nature and can be readily transported to on-site grow locations for immediate processing of freshly harvested cannabis, which dispenses with the need to harvest, transport and process off site. The ability to process "wet" cannabis that is freshly harvested likewise allows for dramatically faster processing that eliminates conventional drying, as discussed above.

The aforementioned steps and devices for performing the same may also be readily arranged to process cannabis in either separate batch processes or by continuous flow. With respect to the latter, and as shown in FIG. 1, each of the steps can be integrated with one another so that freshly harvested cannabis 12 can be immediately fed to a shredder 18, mixed with cold solvent in mixing tank 22 to form a slurry, exposed to ultrasound 26, filtered and treated for chlorophyll removal 28 all in a continuous manner on-site and in immediate proximity to where the cannabis is harvested. The other optional steps, such as French press filtering, secondary biomass treatment with ultrasound and solvent recovery can likewise be readily integrated on-site, and integrated, for example, at the Filter step 28 shown in FIG. 1. As will be readily appreciated by those skilled in the art, the processes of the present invention can be scaled according to a desired weight of cannabis material to be processed for extraction, and can be designed for a given crop or acreage of cannabis harvested provided the parameters and limits of each of the steps described herein are adhered to.

Figure 2:
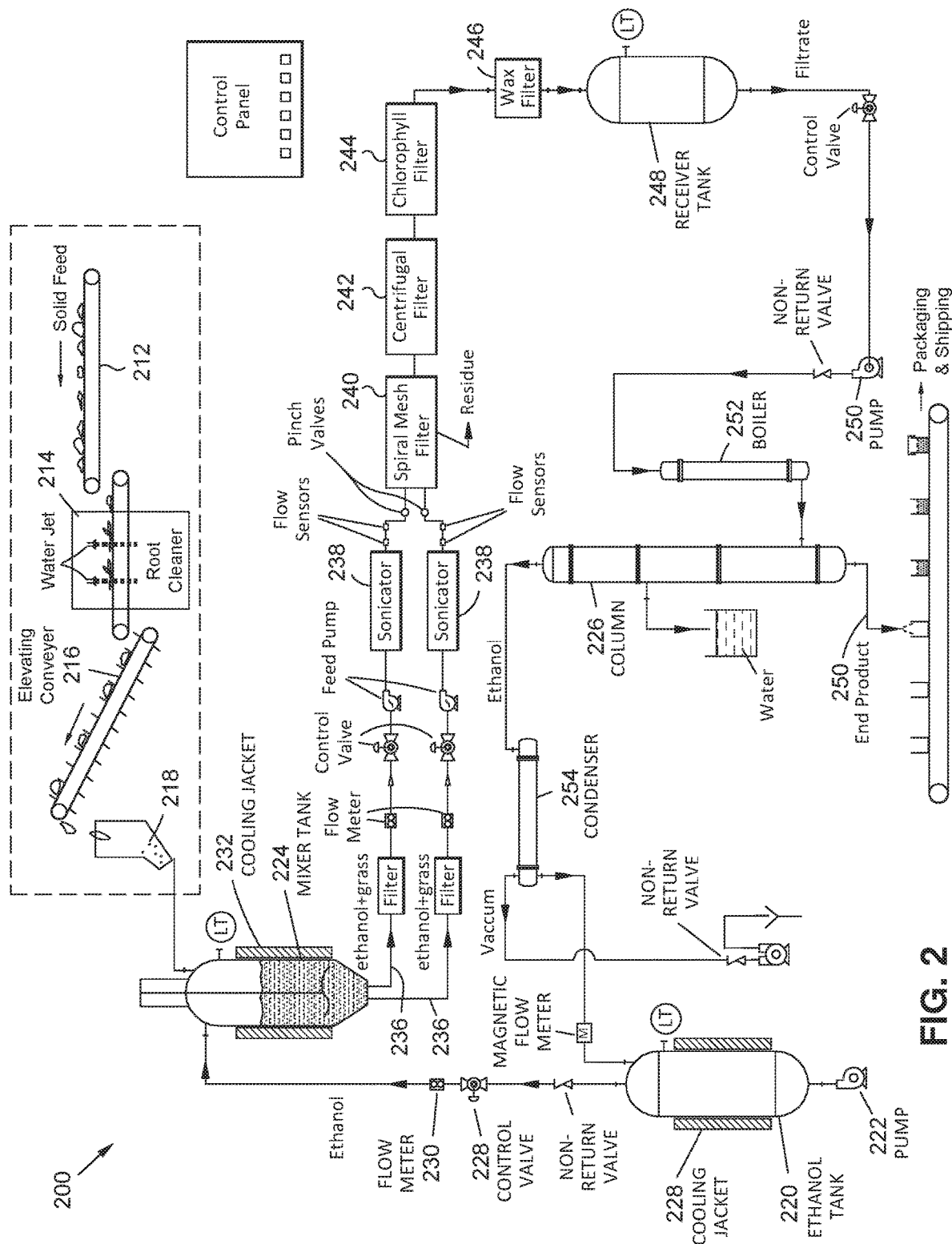
FIG. 2 shows a flow chart of the steps and system components for performing the methods for extracting and concentrating cannabinoids from cannabis per a second embodiment of the present invention.

The extraction technology of the present invention may further be practiced in accordance with a second exemplary system 200 depicted in FIG. 2, to which the following disclosure is directed. As per the aforementioned discussion, the cannabis plant material is shredded to have the desired particulate size, and may include either select portions of the cannabis plant or the entire cannabis plant, including the thicker plant structures such as the roots and stems. To that end, the aforementioned practices discussed above with respect to generating the desired particulate size of plant material may be utilized, including any root-type vegetable washing and processing as may be needed or desired, with elements 212, 214, 216 and 218 corresponding to elements 12, 14 16 and 18 of FIG. 1.

With respect to the various components referenced in FIG. 2, the same are listed below as utilized in connection with an ethanol-based solvent distillation system operative to derive extracts according to the present invention. As per the first embodiment discussed above, the system depicted in FIG. 2 is deemed exceptional at deriving not only extracts from cannabis, but also essential oils and fragrance-based compositions from plant materials as well. With respect to the various components shown and operatively interconnected to one another:

Ethanol tank 220: This is a stainless steel, pharmaceutical grade processing tank having a volume of approximately 2000 liters. Such tank will store ethanol, whereby a pump 222 is connected thereto to pump the required ethanol into a mixer tank 224. The ethanol tank 220 also receives the recovered solvent from the fractionating column (referenced as COLUMN 226), discussed more fully below. The ethanol tank 220 will preferably be filled to capacity before operations, especially when deployed for remote processing. To optimize the extraction process, and in particular to facilitate the effectiveness of the application of ultrasound, and the removal of contaminates such as waxes and the like, it is contemplated that the ethanol tank will be provided with a cooling mechanism, such as a conventional cooling jacket 228 utilizing liquid nitrogen as shown, such that the ethanol stored and distributed therefrom is maintained at a temperature ranging from −40 to −60° C. To that end, it is believed that insulation or other materials necessary to maintain such reduced temperatures will be implemented in connection with the ethanol tank and ethanol delivered therefrom.

The mixer tank 224 is likewise a stainless steel, pharmaceutical grade tank having a volume of approximately 1000 liters that is operatively connected to the output of the aforementioned shredder apparatus 218 discussed above. As illustrated, the shredder/feeder system of components 212, 214, 216 and 218 are mounted on the top thereof, and may optionally be contained within an enclosed environment, shown in broken lines, so as to minimize potential contamination from outside sources. In the exemplary embodiment being discussed, the shredder unit 218 is commercially available and will have a capacity to deliver up to approximately 45 Kg of shredded plant biomass per hour into the mixer tank 224. As discussed above, cryomilling may be utilized in connection with the shredding process to achieve more thorough and uniform particulate formation plus reduce the temperature of the plant material.

As the fresh, shredded plant biomass is fed into the mixer tank 224, ethanol is likewise fed from the ethanol tank 220 in the appropriate proportions, as discussed earlier. To that end, the rate of ethanol fed is controlled by a control valve 228 and flow meter 230, as shown. The ethanol is likewise preferably maintained in a refrigerated state of −40° C. or less, and preferably between −40 and −60° C. as achieved through a cooling mechanism, such as cooling jacket 232 as shown. The shredded biomass and ethanol mixture will be agitated by an impeller fixed atop of mixer tank 224 for a duration extending from thirty seconds to ten minutes and stored in the mixing tank 224 before further processing. Ideally, the mixing tank 224 is designed to be always half empty and is further designed to have a funnel-shape bottom, as shown, to facilitate the flow of the slurry, including any sediment that may be produced as a result of the agitation process, as well as to prevent the introduction of air into the slurry that can negatively impact the application of ultrasound, discussed below.

The slurry of ethanol with plant material will be fed by at least one, but possibly two or more lines for further processing, such as through the two dedicated lines 234, 236 shown in FIG. 2. In this regard, it is believed that having multiple feed lines 234, 236 from the mixer tank 224 will enable the system 200 to run continuously and provide parallel processing, such as when one line may be shut down for maintenance, removing clogs of plant material, and the like, and allowing a second line to continue the slurry to be processed further. As should be understood, however, such multiple lines 234, 236 are optional and provided merely to enable a continuous system to run more reliably by providing redundancy.

Sonicators 238 (or ultrasonic reactor, such as 26 as referred to in FIG. 1) will subject the shredded plant-ethanol slurry fed from the mixing tank 224 to ultra-sonic energy and extract the plant oils into the ethanol solvent as per the earlier discussion above. To that end, such sonicator 238 will deploy ultrasound at a frequency ranging from 5 kHz-1 MHz with the general range of 10 kHz-60 kHz being preferred and with 40 kHz being most preferred. The displacement amplitude will range of from about 20 to 100 micrometers, with 80 micrometers being most preferred. Likewise, the preferred range of power that should be delivered should range from about 90 to about 160 watts per square centimeter of slurry treated. The ultrasonic energy will be applied for a duration ranging from 30 seconds to a maximum of 5 minutes, with up to 120 seconds being preferred. As discussed above, the slurry will be fed to the ultrasound sonication step in a refrigerated state, and should be maintained at a temperature of −40° C. or less so as to minimize the release of wax from the plant material. Also, the use of pinch valves should be utilized at the outlet of the sonicators 238 so as to regulate the internal pressure of the liquid medium that is present for ultrasonic irradiation.

Following the application of ultrasound, it is believed that to derive extracts with the minimum amount of wax and chlorophyll contaminants, the post-ultrasound treated slurry will continue to be refrigerated in the range of −40 to −60° C. so as to allow for the removal of contaminants through conventional winterizing processes. Along those lines, it is believed that in certain applications that the removal of contaminants through winterizing techniques (e.g., removal of solidified wax) can be deployed prior to the application of ultrasound, as may be desired.

Following the step of sonication, a spiral mesh filter 240 is deployed to separate the solid biomass from the liquid component, the latter of which is a mixture of ethanol, water and oils extracted from the cannabis plant. In the embodiment of FIG. 2, such filter 240 will preferably have the capacity to filter approximately 60 liters of slurry per minute. The solid residue component is disposed of while the liquid component flows to the next unit for further processing discussed below. In an optional processing step not shown, such solid residue may further be subjected to a second ultrasound application, as discussed above in the embodiment of FIG. 1, to reduce its mass and thus minimize the volume of waste generated. Such biomass may also be processed for repurposing in a variety of environmentally-friendly applications.

A centrifugal filter 242, which will be of a conventional nature, will next separate the fine particles from the liquid component. In the exemplary embodiment being discussed, the rate of flow through the filter will be approximately 60 liters per minute.

As presently contemplated, a chlorophyll filter 244 will next be sequentially deployed as shown. Such chlorophyll filtering may be achieved through a variety of known techniques and mechanisms known in the art and may likewise include the use of a series of membrane filtration techniques covering microfiltration to remove colloidal matter, tight ultrafiltration or nano-filtration to reduce the color intensity imparted majorly by chlorophyll A and chlorophyll B and to a minor extent by other forms of the coloring matter, with the filtrate being further subjected to activated carbon. In such embodiment, the criteria for selection of membrane separation techniques, going by the molecular weights and sizes of the dissolved components of the extract, will be based on the membrane material as well as the pore sizes having fine distribution and, more importantly, compatibility with the ethanol solvent for extended periods of operation. Such membrane materials believed appropriate for use in the practice of the present invention include polyamide, polyimide, and polyethersulfone and the pore sizes in the form of molecular weight cut-off (MWCO) ranging from 200 Da to 2000 Da. The membranes are tested for the individual component rejection and flux (permeation flow rates across membranes per unit area) to understand the suitability and evaluate the basic performance.

Results based on the indicated membranes showed varying levels of chlorophyll color reduction ranging from approximately 60% to up to 90%. This reduction is believed significant. In this respect, the filtrates with the indicated quantum of color reduction are likely to have that much less issue on the final quality of the product. Tests conducted on the filtrates with activated carbon (AC) showed color free liquid composition, indicating easy removal of the traces of color, if any. The quantity of AC required to remove the traces of remaining, if required, is likely to be fractional as compared to what may be originally needed on the extract without membrane filtration.

Post color removal step, the membrane filtrate is likely to have the original CBD oil intact in the ethanol which only requires desolventization step, discussed below, that leaves improved quality oil as product and ethanol recovered for reuse.

To the extent waxes are not removed earlier through winterization either before or after application of ultrasound and/or if further wax removal is desired or deemed necessary, a conventional wax filtering step 246 may be deployed as shown. Such wax filtering may be achieved through a variety of known techniques and mechanisms known in the art.

Following the sequential removal of biomass and contaminants, the resultant liquid component is fed to receiver tank 248. This, too, is a stainless steel, pharmaceutical grade tank having a volume of preferably up to 1000 liters and operative to store the liquid mixture of ethanol-water-oils following the aforementioned filtration operations. The liquid from this tank 248 is pumped using the pump 250 as shown into the boiler 252, discussed next, before it enters the fractionating column 226 referenced earlier.

The boiler 252 is a stainless steel, pharmaceutical grade, shell and tube heat exchanger which boils the liquid fed thereto using steam. To reduce the temperature necessary to effectuate vaporization of liquid mixture fed thereto, it is contemplated that vacuum distillation methods may be deployed via the boiler 252 whereby the pressure is reduced so that a correspondingly lower boiling temperature can be achieved. To that end, it is believed that utilizing temperatures in the range of 40 to 50° C. and a reduced pressure of 100 mBar or approximately 0.1 atmospheres or less will be optimal. The vapor phase achieved thereby is then sent to the recovery column 226 for separation of water, oil and ethanol, discussed next.

The recovery column 226 is a tall stainless steel, pharmaceutical grade column packed with stainless steel sheets (this is also referred to as a packed fractionating column). This component 226 separates the three liquid components, namely, the water (which becomes introduced into the slurry by virtue of shredding fresh plant material), ethanol and oil. As shown, the water is disposed of, the ethanol is fed to a condenser 254 (discussed next) and subsequently sent to the ethanol tank 220 for reuse. The oil component is collected from the bottom of the column 226 as the end product 256. In the embodiment being discussed, the recovery column 226 is integrated as part of a continuous process and has a capacity of approximately 400 liters per hour.

Condenser 254 is a shell and tube heat exchanger made of pharmaceutical grade stainless steel, just like the other aforementioned components, and has the purpose to condense the ethanol vapors to a liquid phase and send back to the ethanol tank 220. Its construction and operation are conventional and would be readily understood by one of ordinary skill in the art.

Valves, Pipes, Hoses and Flow Meters: As will be appreciated by those skilled in the art, the various valves, pipes, hoses, flow meters and other integrated components will be of a commercially available nature and selected for their appropriate application as would be known to an ordinary artisan. Preferably, whenever available such components will also be fabricated from stainless steel. Because the aforementioned extraction process involves a slurry of particulate plant material suspended in solvent, it will be readily understood and appreciated that the various components of the system should be designed such that there are a minimum of turns, angles, bends, and the like and every effort should made to ensure that the flow path is maintained in as linear as possible, and preferably designed to flow in a downward orientation so as to continuously provide for a gravitational pull of the flow in a downward direction. All such components, and in particular the valves and flow meters, should be operative to accommodate the volumes of fluids flowing therethrough.

Along those lines, flow rates in all non-horizontal sections should be faster than the separation speed, namely, the sedimentation rate by which the solid plant components fall by gravitational pull from the solvent component. As will be appreciated, measurements of the sedimentation rate for all materials (e.g., buds, stems, leaves) should be assessed, as should particle morphology and size, both of which affect separation speed. Ideally, flow in all near-horizontal sections should be fast enough to avoid sedimentation.

It is further believed that the shortest pipe lengths that can be used will further optimize fluid flow and minimize clogging. It should further be appreciated that, whenever possible, components should be utilized that are deemed explosion proof, or D1.1 certified. Likewise, all components should be operative to maintain a consistent flow and pressure of the liquids pass through the systems and all seals should be inspected for full compatibility/resistance to ethanol, water, biomass particles, and low temperatures.

Pumps: As there are hosts of pumps in the market, these components will also be selected using conventional components and selected based upon which is the best suited for the aforementioned applications, as could be determined by one of ordinary skill in the art. To that end, one commercially available pump believed to be ideally suited for the practice of the present invention is the Seepex & MD 1212 produced by SEEPEX GmbH.

Figure 3:
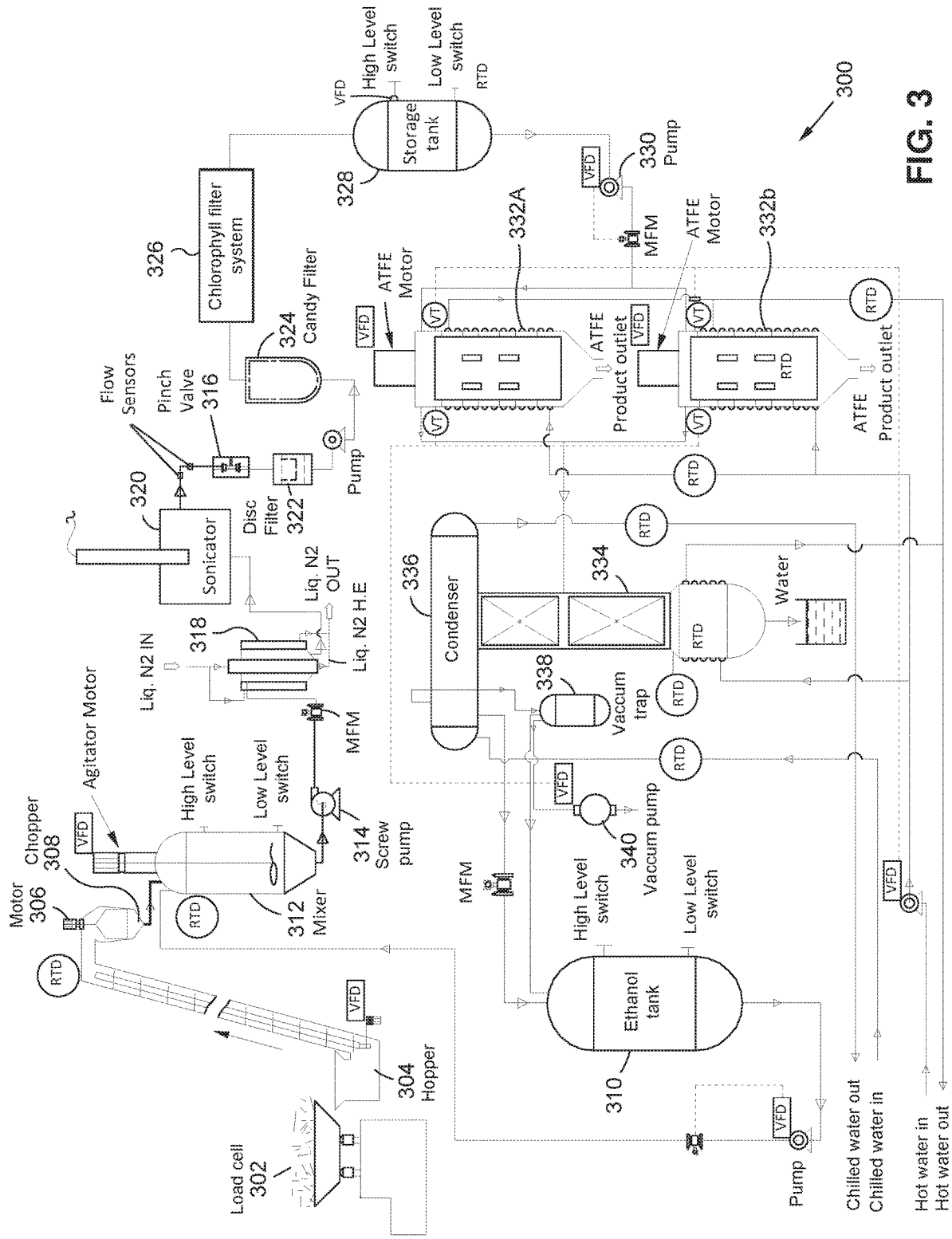
FIG. 3 shows a flow chart of the steps and system components for performing the methods for extracting and concentrating cannabinoids from cannabis per a third embodiment of the present invention.

In yet a further alternative third embodiment shown in FIG. 3, there is depicted system 300 for ultimately deriving the oil-based extracts other than through the boiler and recovery column as shown FIG. 2. In this regard, and as discussed more fully below, such alternative embodiment deploys a wiped film-type evaporator system whereby the filtered slurry, as may be optionally stored in a storage tank 328, is introduced into an Agitated Thin Film Evaporator (ATFE). The ATFE is operative to evenly distribute the filtered slurry over the ATFE's inner surface by an internal rotor. As the product spirals down the wall per gravitational pull, the high-speed rotor tip is operative to generate highly turbulent flow resulting in the formation of bow waves and creating optimum heat flux and mass transfer conditions. The water and ethanol that are present in the product feed are caused to evaporate via conductive heat transfer and ultimately caused to exit a vapor discharge section and thereafter condensed. The non-volatile oil-based components, on the other hand, are discharged at an outlet.

Such system 300, and the methods by which the same are operative to derive the extracts of the present invention is more fully described below. Per the other aforementioned embodiments, cannabis plant material is provided that is shredded to the desired particulate size mentioned above. To that end, system 300 provides a load cell 302 for receiving and holding cannabis plant material that is transferred to hopper 304 and ultimately by a conveyor system, such as a screw-type conveyer or conveyer belt, to chopper 308 driven by motor 306. As per the other aforementioned embodiments, the transfer of the cannabis to chopper 308 may involve the pre-treatment of the cannabis plant material with liquid nitrogen for a duration sufficient so as to freeze the plant material prior to chopping and shredding. Alternatively, treatment with nitrogen can occur as part of a systematic, continuous process where the cannabis or hemp is subjected to liquid nitrogen as part of the transfer process from load cell 302, to hopper 304, and ultimately to chopper 308. In this regard, it is contemplated that the conveyor belt transport may possess a certain length and speed that may coincide with a specific delivery of liquid nitrogen so as to ensure thorough freezing of the plant material prior to being processed into particulate plant materials as may be desired per conventional cryomilling practices.

Once formed to have the desired particulate size, the plant material is fed to mixer 312 into which is also fed ethanol from ethanol tank 310 in a specified range of ratio of ethanol to plant material discussed above, which preferably ranges from 25 mL of ethanol per 10 grams of cannabis to 25 mL of ethanol per 2 to 3 grams of cannabis, with 25 mL to 5 grams typically being deemed most ideal, and mixed for a duration ranging from thirty seconds to ten minutes. In addition, the ethanol provided by ethanol tank 310 will be maintained at a temperature ranging from −40 to −60° C. and maintained at that temperature so that such slurry formed within mixing tank 312 is preferably maintained at a temperature of −40° C. or lower, and preferably in the range of −40 to −60° C. as discussed above. As per the embodiments in FIGS. 1 and 2, the mixer should be formed to have a conical bottom to facilitate slurry flow and reduce sediment build-up/facilitate sediment removal. Care should also be exercised to prevent air from being introduced into the slurry mixture during the step of mixing.

The slurry ultimately formed within mixing tank 312 is pumped by screw pump 314 and refrigerated further in unit 318 whereby liquid nitrogen cools the slurry so as to facilitate the removal of waxes and other components through conventional winterization. As discussed above, in all aspects involving the flow of slurry, the flow rates in all non-horizontal sections should be faster than the separation speed, namely, the sedimentation rate by which the solid plant components fall by gravitational pull from the solvent component. Ideally, flow in all near-horizontal sections should be fast enough to avoid sedimentation.

Thereafter, the slurry is subject to sonic energy provided by sonicator 320. Per the aforementioned embodiments, such ultrasound is preferably applied at a frequency ranging from 5 kHz-1 MHz with the general range of 10 kHz-60 kHz is preferred and 40 kHz being most preferred. Such sonic energy will further be applied with a displacement amplitude in the range from about 20-100 μm, with 80 μm being most preferred, and with power being delivered in the range from 90 to 160 watts per square centimeter of liquid slurry being treated. The ultrasound will further preferably be applied by sonicator 320 for a duration ranging from 30 seconds to a maximum of 5 minutes, with up to 120 seconds being preferred. The slurry is further preferably maintained at a temperature of −40° C. or less when the ultrasound is applied. Importantly, the use of at least one pinch valve 316 should be deployed on the outlet side of the sonicator 320 to regulate the internal pressure therein where the liquid medium is present for ultrasonic irradiation.

The post-sonicated slurry is then fed to a coarse disc filter 322 that is operative to facilitate the removal of a portion of the solid biomass portion from the liquid component of the slurry and likewise act as a dewatering system that will squeeze out the biomass and separate the solids and the liquid. Although not shown, such filter 322 is preferably deployed as a multi-disk screw filter press that has a central screw with fixed and rotating disks around the screw. Ideally, the flow rate for such filter 322 will be 1.5-3.0 liters per minute.

A pump then further causes the liquid component of the slurry to pass to candy filter or pressure filter 324 for further filtration to remove remaining biomass from the liquid component of the slurry. According to a preferred embodiment, such filter 324 will have a cloth filter medium with a 1 micron opening. This will remove all the slurry plant particles up to 1 micron size. Per disc filter 322, the candy filter will be operative to accommodate a flow rate of 1.5-3.0 liters per minute. As per the other aforementioned embodiments, to the extent the biomass is isolated from the slurry, the same may be treated further with ultrasound to produce a lesser volume of biomass or, alternatively, the biomass may be repurposed for other environment-friendly applications.

The liquid portion of the slurry is then fed to a chlorophyll filter system 326 that is operative to remove the chlorophyll present in the liquid portion of the slurry fed thereto. To that end, it is contemplated that chlorophyll filter system 326 will be operative to remove the chlorophyll by any of a variety of methods known in the art. Likewise contemplated are the mechanisms for removing chlorophyll as discussed above in connection with the embodiment of FIG. 2 whereby a series of membrane filtration techniques are deployed, in combination with and activated carbon, that cover microfiltration to remove colloidal matter, tight ultrafiltration or nanofiltration to reduce the color intensity imparted majorly by chlorophyll A and chlorophyll B and to a minor extent by other forms of the coloring matter. Such membrane materials may be selected from the group consisting of polyamide, polyimide, and polyethersulfone having pore sizes in the molecular weight cut-off (MWCO) range from 200 Da to 2000 Da. Advantageously, the subsequently produced filtrates, when further treated with activated carbon (AC) showed color free liquid composition, indicating easy removal of the traces of color, if any. The quantity of activated carbon required to remove the traces of remaining, if required, is likely to be fractional as compared to what may be originally needed on the extract without membrane filtration.

Following the removal of chlorophyll, the liquid component is fed to storage tank 328, which is then fed by pump 330 to the ATFE systems 332A, 332B. ATFEs 332A, 332B are essentially operative to extract solvent (i.e., ethanol alone and/or the combination of water and ethanol) at low temperature using vacuum evaporation at a temperature preferably below 50° C. To that end, each ATFE 332A, 332B will be constructed to perform wiped-film evaporative oil-solvent separation processes and will include a vertical cylinder with a central shaft with blades fixed and in close contact with the inner wall of the cylinder. Each ATFE 332A, 332B likewise has two drums, with one outer heated drum, on the inside of which the thin film is formed, and an inner drum within which is disposed a central shaft on which the wiper blades are fixed. The inner rotor drum is empty and can be filled with moisture adsorbing molecular sieves to make a packed bed. The ethanol-water mixture vapor can be made to pass through this packed bed column, and dry vapor made to come out. Moreover, per conventional wiped-film separation techniques, the cylinder is operative to be heated to a suitable temperature. The central shaft is connected to a motor and rotates at high speed, and the blades scraping the inner walls of the cylinder when a liquid is distributed along the inner wall of the cylinder, the blades scrape it and forms a thin film on the heated cylinder wall. The cylinder is connected to a vacuum pump which sucks out all the vapors that form when the thin film is heated. Ultimately, the vapors of ethanol and/or ethanol and water will escape out where as the oil component containing the cannabinoids, which will have a higher boiling point, will not evaporate and trickles down along the cylinder wall and is collected at the bottom (product outlet).

According to the present invention, each ATFE will be sized and constructed to treat and separate a maximum of 8000 liters of liquid (mixture of ethanol, water and oil) in 20 hours. To that end, each ATFE 332A, 332B preferably has a diameter of approximately 0.9 m and a height of 3 m, and each will have a surface area of 7 sq. meters and operative to have an operating temperature of 40 to 50° C. under a pressure of 50 mm Hg. According to such embodiment, the flow rate of liquid fed to the ATFEs 332A, 332B will be approximately 400 liters per hour. Advantageously, such system has a capacity to process 1000 Kgs./day of fresh cannabis plant biomass and generate oil production of approximately 27 Kgs./day. Moreover, as will be appreciated by those skilled in the art, by removing the solvent component via a low temperature process thus it avoids any degradation of the cannabinoids due to heat. Moreover, it is a continuous process and can be further scaled up. Perhaps most advantageous, however, is the fact that the ATFEs 332A, 332B are operative to remove both water (emanating from the shredded cannabis plant) and solvent together from the oil extract and thus enable freshly harvested plant materials with a high water content to be processed immediately without the need for drying or having to dehydrate the plant material as so many other conventional processes must do.

As shown, in order to achieve optimal production, there are preferably at least two such systems 332A, 332B installed as part of system 300. While one ATFE is operating, the respective other second one will be getting regenerated under high vacuum. The cooling effect due to evaporative cooling can be used to condense the ethanol/water vapors from first packed bed. Thus, by alternating between the two systems 332A, 332B, there can be a continuous operation.

Once the ATFEs 332A, 332B separate the ethanol-water vapors from the oil, and the oil is collected at the bottom of the ATFE as shown and discussed above, the ethanol-water vapors pass through a fractionating column 334 where ethanol is separated from the water and condensed in condenser 336, per conventional mechanisms known in the art. The ethanol is then collected through vacuum recovery per vacuum trap 338 driven by vacuum pump 340 and recycled back to ethanol tank 310. Water produced from the ethanol water separation in the fractionation column 334 is discarded.

As will be furthered appreciated by those skilled in the art, it will be understood that all of the aforementioned systems disclosed in connection with FIGS. 1-3 will incorporate electrical and electronics components operative to control the extraction processes and monitor all systems parameters, such as plant mass weight, speed, temperatures, flow rate, vacuum pressures and the like. To that end, and as shown by way of example in FIG. 3, it is contemplated that at multiple points throughout the processing flow path that various pumps, switches, liquid inlets and outlets and the like will be provided. Further integrated with such control systems include resistance thermometers or resistance temperature detectors, identified as RTD, that are deployed to measure the temperature utilizing known, conventional technology. Likewise, deployed are magnetic flow meters, represented as MFM, for monitoring the rate of fluid flow; variable frequency drives, referenced as VFD, for adjusting motor speed and torque as may be desired at a particular points in the processing; and vacuum transmitters, shown as VT, for accurately measuring pressures and vacuum ranges, particularly with respect to the operation of the ATFEs 332A, 332B shown in FIG. 3. All such controls are well-known in the art and can be readily deployed by one of ordinary skill.

Figure 4:
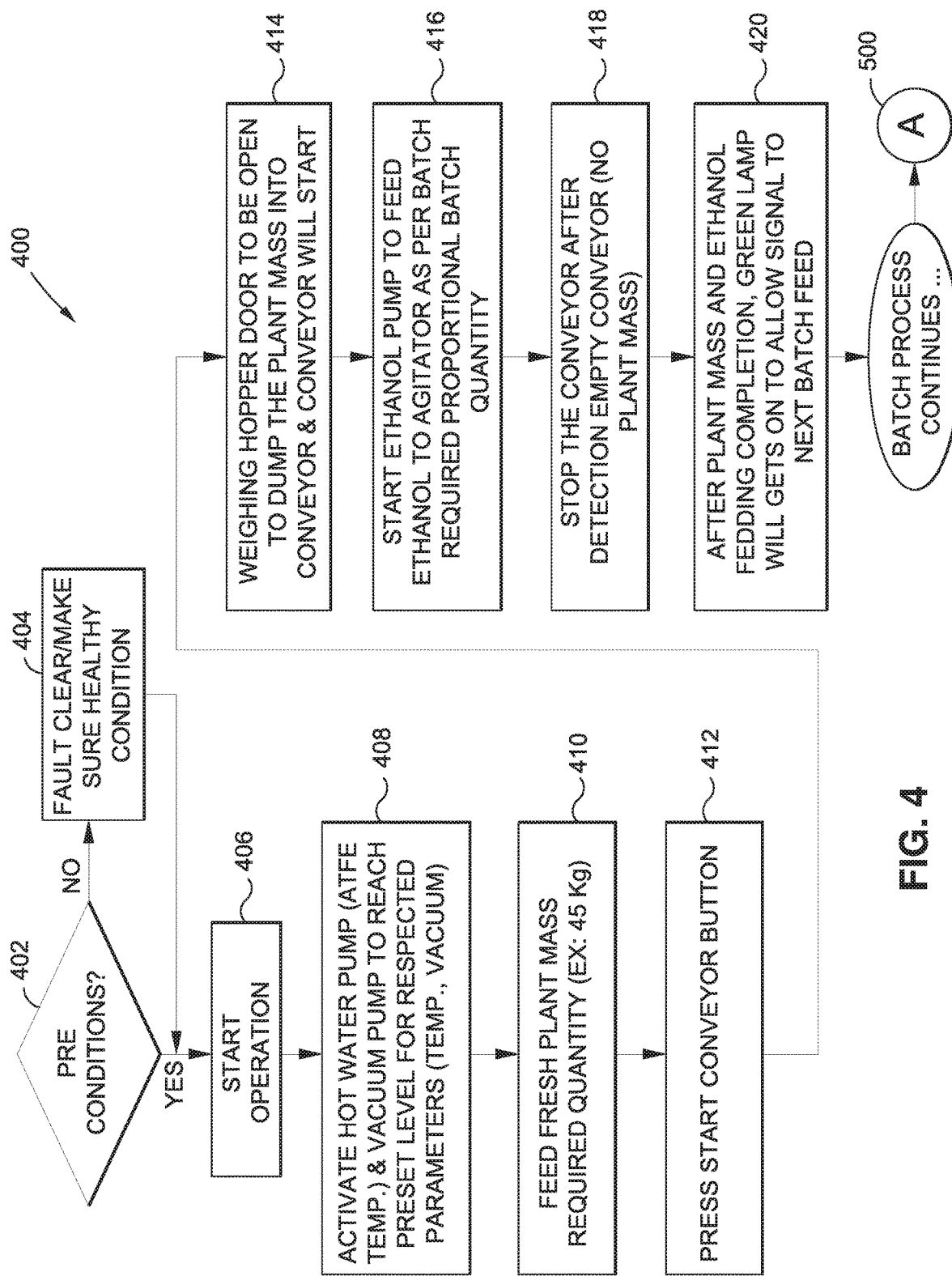
FIG. 4 depicts the first portion of a flow chart for controlling and monitoring the systems and methods of the present invention for the automated and continuous production of cannabinoids of the present invention.
Figure 5:
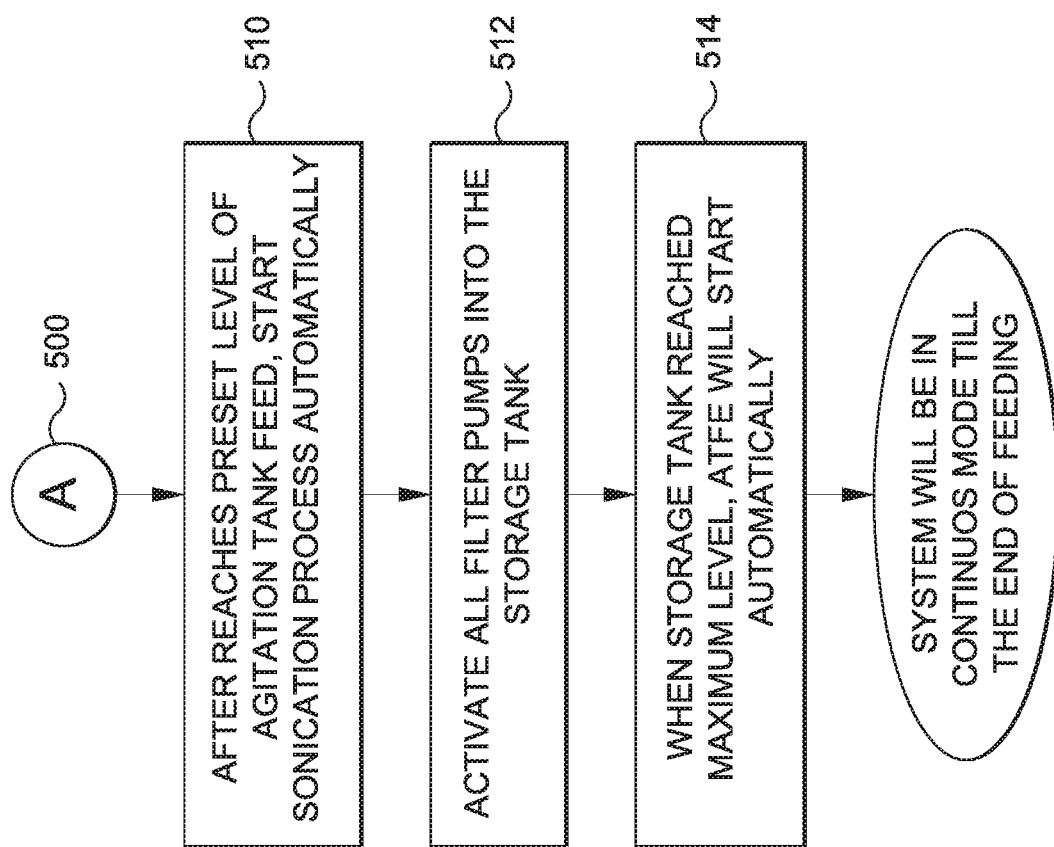
FIG. 5 depicts the remaining portion of the flow chart originating in FIG. 4.

In the context of the present invention, there is further shown in FIGS. 4 and 5 a process 400 by which the systems of the present invention may be systematically operated for optimal and reproducible extract production. According to such process 400, an initial assessment is made as to whether specific preconditions for proper processing are met 402. In this regard, such preconditions include confirmation that each of the respective components is in operative working order, all hoses and connections are clear and not clogged, and an adequate supply of all necessary materials, including reserves of ethanol, liquid nitrogen, and the like are all provided and readily accessible. To the extent any deficiencies exist, the same are addressed in step 404 per conventional troubleshooting and maintenance. In some cases, it may be deemed optimal to test any of the aforementioned systems shown in FIGS. 1-3 with clear tap water to possibly identify the location of any leaks, which may then be followed by running the system with water and chopped greens to identify any potential hydraulic issues. Thereafter, if necessary, the systems should be test operated with ethanol and then eventually ethanol with cannabis.

Once proper operation of the entire system is confirmed, operation starts at 406 followed by step 408, which applies to the system shown in FIG. 3 whereby the ATFE systems are activated such that the same are operative to perform the wipe-film evaporated process within the heating and the vacuum parameters disclosed above as required for proper operation.

Thereafter, a confirmed quantity of cannabis is provided and made readily available in step 410 that will be subsequently conveyed by conveyor process 412 in an appropriate weight and at an appropriate rate per step 414 to the mixing tank discussed in each of the aforementioned systems. Such step 414 may further involve the integrated treatment of the conveyed plant material with liquid nitrogen in amounts suitable to facilitate cryomilling applications.

Concurrently with the delivery of the plant material, the ethanol will be fed to the mixing tank and the proportional amounts discussed as discussed above such that the ratio of solvent to plant material is appropriately maintained. Once the mixing tank has been provided with adequate amounts of solvent and plant material in the desired rations, the conveyer process stops at 418 and mixing allowed to continue in the mixing tank for an appropriate duration as identified in step 420, the latter being tied to a signal, such as a green light, operative to indicate when the slurry has been formed and is ready for further processing. The process 400 then proceeds by A 500 to FIG. 5 whereby the slurry, once sufficiently mixed, is fed to the sonication processor that is operative to automatically deliver a sufficient degree of ultrasonic energy to the appropriate volumes of slurry passing therethrough 510. To that end, all systems should be maintained so as to eliminate any feed of air pockets, foam or bubbles, into the ultrasound processor, and care must be taken to check for vortexes and trapped gas in any of the biomass solids. As it will be appreciated by those skilled in the art, trapped gases in any biomass can adversely affect the application of ultrasound and possibly damage the ultrasound equipment.

Following the application of the ultrasound 510, operators of the present invention will activate all filter pumps to facilitate the removal of contaminates and biowaste, in particular any materials removed by winterization and the proper extraction and isolation of biomass.

Following the activation of the filter pumps in step 512, and once the storage tank, in reference to the system of FIG. 3, has reached a requisite volume, the activation of the solvent extraction may be deployed, in particular the introduction of the liquid component of the slurry to the ATFE at step 514 as may be controlled by various pumps, flow rate monitors, vacuum transmitters, and temperature sensors such that the final extract and the solvents removed therefrom are all generated and separated in conformance with all of the aforementioned parameters, including but not limited to volumes of fluid, temperature ranges, specified vacuum pressures and the like.

Advantageously, the aforementioned systems shown and described are capable of being designed and configured to operate as a standalone system or may be mounted on a truck or flatbed, such as a mobile skid, so as to be mobile in nature and operative to be deployed for remote processing, such as at farming operations to allow extracts to be generated on-sire immediately after harvesting. In such applications, it is contemplated that a reserve of ethanol should be kept on hand and made available. To that end, it is suggested that a separate tanker (about 3000 liters) filled with ethanol should accompany the mobile system.

In all cases, the ultimate extracts derived by the processes of the present invention have an exceptionally high concentration of cannabinoids, and in particular CBDs that can be quantified by UV-vis absorbent spectroscopy and other known methods. Quite unexpectedly, the methods of the present invention are operative to derive extracts having approximately 70% greater concentration of desired cannabinoids than conventional extraction methods. For any given particular extract, the speciation of the cannabinoid of interest and its relative abundance can be determined through conventional analytical techniques such as GCMS and NMR. To the extent a particular cannabinoid is of interest, the same may be further isolated using known techniques and subsequently utilized to derive therapeutic compositions, as well as processed for administration to individuals. Any specific cannabinoids so isolated may further be molecularly modified to produce cannabinoid derivatives useful to treat a particular condition such as anxiety, dementia or any of many other specific conditions.

To that end, it is contemplated that CBDs isolated through the extracts of the present invention may further be modified, for example, to motivate localization at targeted areas of treatment. Hydroxylations, or additions of other carboxylates, for instance, will mechanically drive the efficiency in CBDs crossing the blood brain barrier (BBB). These modifications can be accomplished through such synthetic chemistry techniques as markovnikov addition of leaving groups directed at the olefins for nucleophilic addition of functional groups. The resulting CBD derivatives are stable, therapeutically relevant pharmaceutical compositions having greater bioavailability and efficacy than naturally-derived cannabinoids due to the ability of such compositions to be more hydrophilic in nature and operative to be more readily absorbed systemically than the naturally-occurring molecular forms from which they are derived. As will be appreciated by those skilled in the art, any of a variety of modifications may be made to derive cannabinoid-based compositions operative to produce a desired therapeutic effect.

Additional modifications and improvements of the present invention may also be apparent to those of ordinary skill in the art. Along those lines, and as discussed above, the methods of the present invention may be operatively deployed to extract other target cannabinoids or combinations of cannabinoids, including any or all of the following cannabinoids and their derivatives: Cannabigerolic Acid (CBGA); Cannabigerolic Acid Monoethylether (CBGAM); Cannabigerolic (CBG); Cannabigerolic Monoethylether (CBGM); Cannabigerovarinic Acid (CBGVA); Cannabigerovarin (CBGV); Cannibichromenic Acid (CBCA); Cannibichromene (CBC); Cannibichromevarinic Acid (CBCVA); Cannibichromevarin (CBCV); Cannabidiolic Acid (CBDA); Cannabidiol Monoethylether; Cannabidiol-C4 (CBD-C4); Cannabidivarinic Acid (CBDVA); Cannabidivarin (CBDV); Cannabidiorcol (CBS-C1); Delta-9-tetrahyrocannabinolic Acid A (INPLANTA A-A); Delta-9-tetrahyrocannabinolic Acid B (INPLANTA A-B); Delta-9-tetrahyrocannabinol (INPLANTA); Delta-9-tetrahyrocannabinol-C4 (INPLANTA-C4); Delta-9-tetrahyrocannabivarin (INPLANTA V); Delta-9-tetrahyrocannabiorcolic Acid (INPLANTA A-C1); Delta-9-tetrahyrocannabiorcol (INPLANTA-C1); Delta-7-cis-iso-tetrahyrocannbivarin; Delta-8-tetrahyrocannabinolic Acid (8-INPLANTA A); Delta-8-tetrahyrocannabinol (8-INPLANTA); Cannabicyclolic Acid (CBLA); Cannabicyclol (CBL); Cannabicyclovarin (CBLV); Cannabielsoic Acid A (CBEA-A); Cannabielsoic Acid B (CBEA-B); Cannabielsoin (CBE); Cannabinolic Acid (CBNA); Cannabinol (CBN); Cannabinol Methylether (CBNM); Cannabinol-C4 (CBN-C4); Cannabivarin (CBV); Cannabinol-C2 (CBN-C2); Cannabiorcol (CBN-C1); Cannabinodiol (CBND); Cannabinodivarin (CBVD); Cannabitriol (CBT); 10-Ethoxy-9-hydroxy-delta-6a-tetrahyrocannabinol; 8,9-Dihydroxy-delta-6a-tetrahyrocannabinol; Cannabitriolvarin (CBTV); Ethoxy-cannabitriolvarin (CBTVE); Dehydrocannabifuran (DCBF); Cannabifuran (CBF); Cannabichromanon (CBCN); Cannabicitran (CBT); 10-Oxo-delta-6a-tetrahyrocannabinol (OINPLANTA); Delta-9-cis-tetrahydrocannbinol (cis-INPLANTA); 3,4,5,6-Tetrahydro-7-hydroxy-alpha-alpha-2-trimethyl-9-n-propyl-2,6-methano-2H-1-benzoxocin-5-methanol (OH-iso-HHCV); Cannabiripsol (CBR); and Trihydroxy-delta-9-tetrahyrdo-cannabinol (triOH-INPLANTA).

In addition to extracting cannabinoids from cannabis, it is contemplated that the systems and methods of the present invention are exceptionally effective in deriving essential oils and fragrance-based compounds from plant materials, as would be readily understood by those skilled in the art. In this regard, the systems and methods of the present invention may be readily utilized to derive extracts from rose, lavender and other fragrant botanicals, especially by utilizing the cold ethanol processes discussed at length above. Thus, the particular combination of parts and steps described and illustrated herein is intended to represent only certain embodiments of the present invention, and is not intended to serve as limitations of alternative devices and methods within the spirit and scope of the invention.

The following examples and representative procedures illustrating ultrasound based extraction of CBDs from plant material in accordance with the present teachings, and are likewise provided solely by way of illustration. They are not intended to limit the scope of the appended claims or their equivalents.

The following samples were treated with ultrasound at the following conditions:

TABLE 1-1

List of samples, solvent conditions and test parameters.

| Sample | Solvent | Volume (mL) | Temperature (° C.) | Type of Sample | Mass (grams) | Ultrasound/ Incubation Time | Amplitude |
|---|---|---|---|---|---|---|---|
| 1 | Ethanol | 250 | 26 | Bud | 50 | 30 seconds | 80 |
| 4 | Ethanol | 250 | 26 | Bud | 50 | 120 seconds | 80 |
| 7 | Ethanol | 250 | 26 | Bud | 50 | 300 seconds | 80 |
| 24 | Ethanol | 250 | 26 | Bud | 50 | 2 minutes | — |
| 25 | Ethanol | 250 | 26 | Leaves/stems | 50 | 2 minutes | — |

TABLE 1-1-continued

List of samples, solvent conditions and test parameters.

| Sample | Solvent | Volume (mL) | Temperature (° C.) | Type of Sample | Mass (grams) | Ultrasound/ Incubation Time | Amplitude |
|---|---|---|---|---|---|---|---|
| 12 | Ethanol | 250 | 26 | Bud | 50 | 120 seconds | 20 |
| 13 | Ethanol | 250 | 26 | Bud | 50 | 120 seconds | 60 |
| 11 | Ethanol | 250 | 26 | Bud | 50 | 120 seconds | 80 |
| 14 | Ethanol | 250 | 26 | Bud | 50 | 120 seconds | 100 |
| 6 | Ethanol | 250 | 26 | Roots | 50 | 120 seconds | 80 |
| 26 | Ethanol | 250 | 26 | Roots | 50 | 2 minutes | — |

All samples were filtered and evaluated for CBD content by UV-Visible spectroscopy. From these conditions, we determined that liquid phase extraction of CBDs from plant materials by ultrasound is 30-100% greater in efficiency than traditional extraction methods.

1.2 Filtering and Preparation of CBD Extracts from Biomass (Plant Material)

Following ultrasound, or incubation, of ethanol-submerged biomass material (bud, leaves/stems, and root), the CBD-depleted biomass was filtered out by a course filter (100 µm). The resultant filtrate was passed through a second gravimetric filter (10 µm). The resultant filtrate was transparent and still contained chlorophyll.

To a 500 mL round bottom flask, 250 mL of sample #1 was placed on a rotary evaporator (rotovap) to remove the ethanol. Once the ethanol was evaporated off the sample, the oil extract still contained water. It was determined that the fresh biomass material still contained water. To remove the water from sample #1, 3 grams of magnesium sulfate was added to the oil extract and incubated at room temperature (−26° C.) for 15 minutes. Following this incubation step, 20 mL of 100% ethanol was added to the oil extract, and passed through a 0.2 µm filter to remove the magnesium sulfate. The resulting filtrate was placed on the rotovap to remove the remaining ethanol. Once complete, the resulting material was an oil extract-containing carboxylated CBDs.

1.3 Quantitative Analysis of the CBD Extracts by UV-Visible Spectroscopy

Figure 6:
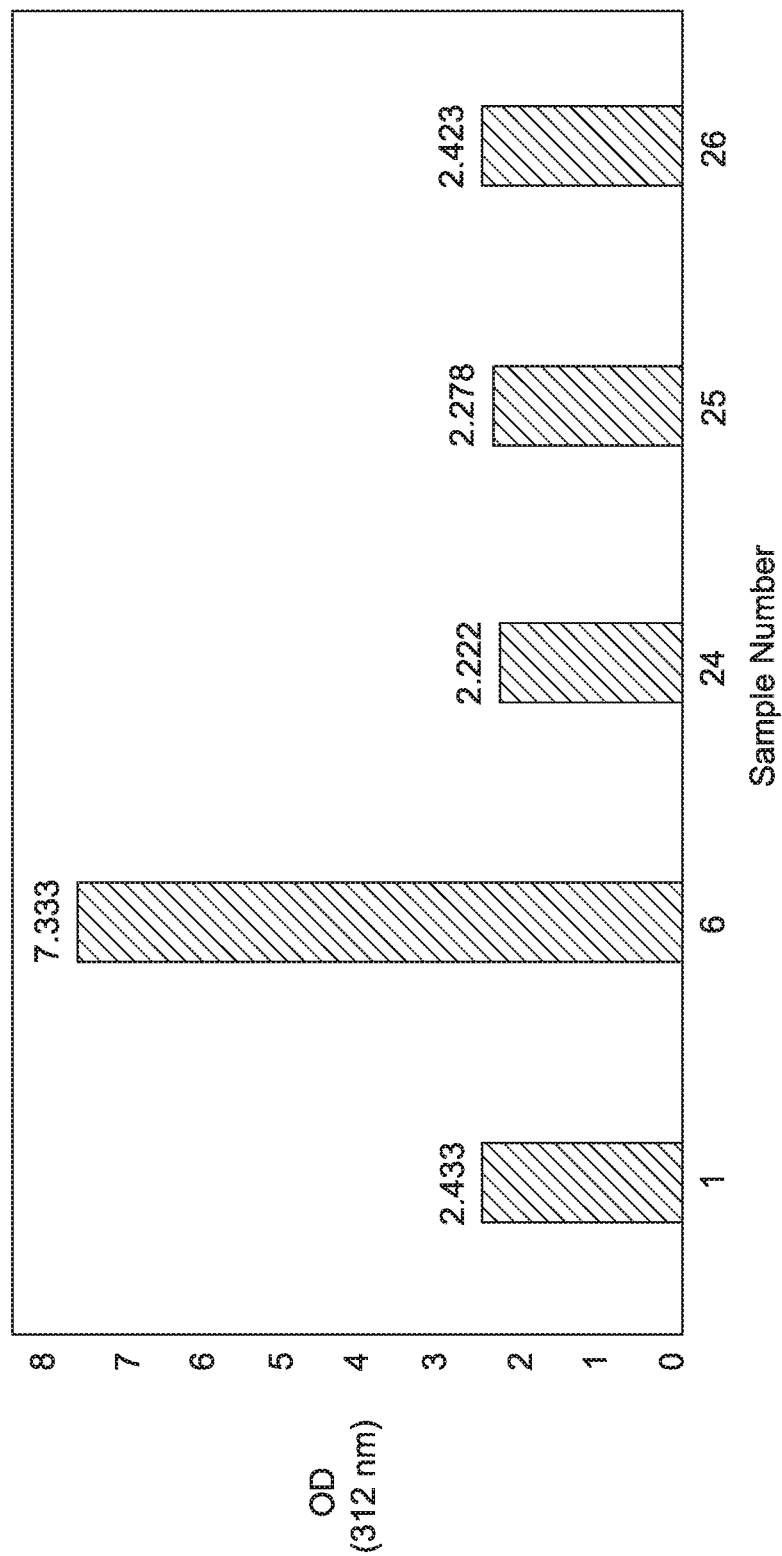
FIG. 6 illustrates absorbance of CBD extracts derived using the methods of the present invention at 312 nm by UV-visible spectroscopy.

To the prepared oil extract, a 50 mL volume of 100% ethanol was added to each sample from Table 1-1. Once the oil extract is diluted in ethanol, this makes handling the material easier. To a quartz cuvette, we added 500 µL of ethanol-containing oil extract to 2.5 mL of 100% ethanol. For sample #6, we added 250 µL of ethanol-containing oil extract to 2.75 mL of 100% ethanol. These steps were taken to dilute the sample for adequate detection. Each sample was measured for absorbance at 312 nm wavelength. Measuring the absorbance at 312 nm is inclusive to 90% of the known therapeutically relevant CBDs. As shown in FIG. 6, which shows Absorbance of CBD extracts at 312 nm by UV-visible spectroscopy, in comparing traditional extractions of bud, leaves/stems, and roots (samples #24, #25, and #26) to the use of ultrasound there is a greater than 2-fold increase in CBD content for sample #6. For sample #1, there is still a significant increase in content over the traditionally extracted samples. In conclusion, these data indicate that ultrasound is an ideal mechanism for extracting therapeutically relevant CBDs from plant materials.

What is claimed is:

1. A method for extracting and concentrating CBD from hemp plant material comprising the steps:
   a) harvesting a hemp plant from which said hemp plant material is derived;
   b) shredding or grinding said harvested plant in step a) to produce particulate hemp plant material;
   c) mixing said particulate hemp plant material in step b) with an ethanol solvent to form a slurry;
   d) subjecting said slurry produced in step c) to ultrasonic energy, said ultrasonic energy being applied at a frequency ranging from 5 kHz-1 MHz and having a displacement amplitude in the range from about 20 to 100 mm with power being delivered to said slurry in a range from about 90 to about 160 watts per square centimeter of slurry treated, said ultrasound being applied for a duration ranging from 30 seconds to 5 minutes;
   e) filtering said slurry treated with ultrasound in step d) to remove wax, biomass and chlorophyll to derive a liquid extract; and
   f) treating said extract produced in step e) to remove water emanating from said hemp plant shredded in step b) and residual ethanol solvent introduced in step c) to produce a concentrated resultant extract.

2. The method of claim 1 wherein in step b), said hemp plant material is shredded or grinded to have a particle size ranging from 1 to 12 mm.

3. The method of claim 2 wherein said particle size ranges from 2 to 6 mm.

4. The method of claim 1 wherein in step b) said particulate hemp plant material is shredded or grinded to have a particle size operative to pass through a 0.5 inch mesh screen.

5. The method of claim 4 wherein said particulate hemp plant material is operative to pass through a 0.25 inch mesh screen.

6. The method of claim 1 wherein in step c), the amount of ethanol solvent added to particulate hemp plant material will range from 25 mL of ethanol solvent per 50 grams of particulate hemp plant material to 25 mL of ethanol solvent per 0.1 gram of particulate hemp plant material.

7. The method of claim 6 wherein in step c), the ratio of ethanol solvent to hemp plant material ranges from 25 mL of ethanol solvent per 10 grams of particulate hemp plant material to 25 mL of ethanol solvent per 2 grams of particulate hemp plant material.

8. The method of claim 7 wherein step c), the range of ethanol solvent to particulate hemp plant material will range from 25 mL of ethanol solvent per 10 grams of particulate hemp plant material to 25 mL of ethanol solvent per 5 grams of particulate hemp plant material.

9. The method of claim 1 wherein said ethanol solvent is maintained at a temperature of around −40 to −60° C. when mixed with said particulate hemp plant material to form said slurry.

10. The method of claim 1 wherein in step d), said ultrasound is applied at a frequency ranging from 10 kHz to 60 kHz.

11. The method of claim 10 wherein said ultrasound is applied at a frequency of 40 kHz.

12. The method of claim 1 wherein said ultrasound possesses a displacement amplitude of 80 mm.

13. The method of claim 1 wherein in step d), said ultrasound is applied for a duration ranging from 30 seconds to 120 seconds.

14. The method of claim 1 wherein step e) further comprises at least partially removing and further subjecting said biomass to ultrasound for a time, duration, frequency, and power sufficient to reduce the mass of said biomass.

15. The method of claim 1 wherein step e) further comprises recovering and recycling ethanol solvent from said post-ultrasound treated slurry.

16. The method of claim 14 wherein step e) further comprises applying ultrasonic radiation at a frequency ranging from 35 to 130 kHz for a duration ranging from 5 to 20 minutes and at an intensity of 50-60 watts per square centimeter.

17. A method for extracting and concentrating CBD from hemp plant material comprising the steps:
  a) harvesting a hemp plant from which said hemp plant material is derived;
  b) shredding or grinding said harvested plant in step a) to produce particulate plant material;
  c) mixing said particulate plant material in step b) with an ethanol solvent to form a slurry;
  d) subjecting said slurry produced in step c) to ultrasonic energy, said ultrasonic energy being applied at a frequency ranging from 5 kHz-1 MHz and having a displacement amplitude in the range from about 20 to 100 mm with power being delivered to said slurry in a range from about 90 to about 160 watts per square centimeter of slurry treated, said ultrasound being applied for a duration ranging from 30 seconds to 5 minutes; and
  e) sequentially filtering said slurry produced in step d) to remove biomass, chlorophyll and wax to derive a liquid extract; and
  f) heating said extract produced in step e) to vaporize and separate water emanating from said hemp plant shredded in step b), and ethanol solvent introduced in step c) to isolate a concentrated resultant extract.

18. The method of claim 17 wherein in step b) said plant material is shredded or grinded to have a particle size operative to pass through a 0.5 inch mesh screen.

19. The method of claim 17 wherein in step c) said ethanol solvent has a temperature of −40° C. or less.

20. The method of claim 17 wherein step f) further comprises reducing the pressure while concurrently heating said extract.

21. The method of claim 20 wherein step f) comprises wiped-film evaporative oil-solvent separation.

22. The method of claim 21 wherein in step e), said chlorophyll is removed by the sequential application of membrane filtration and activated carbon.

* * * * *